United States Patent
Lin et al.

(10) Patent No.: US 11,596,362 B2
(45) Date of Patent: Mar. 7, 2023

(54) METHOD AND SYSTEM FOR QUICKLY DETECTING AN ABNORMAL CONCENTRATION OF POTASSIUM IONS IN BLOOD FROM AN ELECTROCARDIOGRAM

(71) Applicant: National Defense Medical Center, Taichung (TW)

(72) Inventors: Shih-Hua Lin, Taipei (TW); Chin-Sheng Lin, Taipei (TW); Chin Lin, Taipei (TW)

(73) Assignee: National Defense Medical Center, Taichung (TW)

( * ) Notice: Subject to any disclaimer, the term of this patent is extended or adjusted under 35 U.S.C. 154(b) by 215 days.

(21) Appl. No.: 16/910,035

(22) Filed: Jun. 23, 2020

(65) Prior Publication Data

US 2021/0290180 A1    Sep. 23, 2021

(30) Foreign Application Priority Data

Mar. 17, 2020    (TW) ................................ 109108808

(51) Int. Cl.
*A61B 5/00*    (2006.01)
*A61B 5/145*   (2006.01)
*A61B 5/332*   (2021.01)

(52) U.S. Cl.
CPC .......... *A61B 5/7278* (2013.01); *A61B 5/0006* (2013.01); *A61B 5/14546* (2013.01);
(Continued)

(58) Field of Classification Search
CPC ............ A61B 5/318; A61B 5/346–366; A61B 5/7264; A61B 5/0006; A61B 5/14546;
(Continued)

(56) References Cited

U.S. PATENT DOCUMENTS

2018/0233227 A1*  8/2018  Galloway ............ G06N 3/0445
2018/0350468 A1* 12/2018  Friedman ........... A61B 5/14546

* cited by examiner

*Primary Examiner* — Scott M. Getzow
(74) *Attorney, Agent, or Firm* — Bruce Stone LLP; Joseph A. Bruce

(57) ABSTRACT

A method and system are devised for quickly detecting an abnormal concentration of potassium ions in blood from an electrocardiogram. The system includes at least one vector-converting device that includes a processor, a transmitter, at least one memory and at least one storage unit. The at least one storage includes a model data module and a predicting and converting module. The model data module includes data of a model of the concentration of potassium in the blood. The model of the concentration of potassium in the blood includes at least one reference electrocardiogram and corresponding reference data of the concentration of potassium in the blood. The predicting and converting module converts an electrocardiogram into a corresponding predicted concentration of potassium in the blood according to the reference concentration of potassium in blood. The vector conversions device is connected to at least one electrocardiogram generator and at least one monitor. Thus, the electrocardiogram obtained by the electrocardiogram generator is converted to the corresponding predicted concentration of potassium in the blood. The corresponding predicted concentration of potassium in the blood is shown on a monitor to facilitate the medical personnel to take proper actions to reduce the risks of sudden cardiac death.

19 Claims, 9 Drawing Sheets

(52) U.S. Cl.
CPC ............ *A61B 5/332* (2021.01); *A61B 5/7267* (2013.01); *A61B 5/7275* (2013.01); *A61B 2562/222* (2013.01)

(58) Field of Classification Search
CPC ..... A61B 5/332; A61B 5/7267; A61B 5/7275; A61B 2562/222
See application file for complete search history.

METHOD AND SYSTEM FOR QUICKLY DETECTING AN ABNORMAL CONCENTRATION OF POTASSIUM IONS IN BLOOD FROM AN ELECTROCARDIOGRAM

BACKGROUND OF INVENTION

1. Field of Invention

The present inventions relates to detections of potassium ions and, more particularly, to a method for quickly detecting an abnormal concentration of potassium ions in blood from an electrocardiogram.

Related Prior Art

Patients of different diseases exhibit different physiological reactions to different concentrations of potassium ions in blood. A normal concentration of potassium ions in blood is about 3.5 to 5.0 meq/L. Hyperkalemia is diagnosed when the concentration of potassium ions in blood is higher than 5.1 meq/L. Hypokalemia is diagnosed when the concentration of potassium ions in blood is lower than 3.5 meq/L. A patient tends to feel powerless and his or her pulse tends to slow down when the concentration of potassium ions in his or her blood rises to 7 meq/L for example. Risk of sudden death of the patient because his or her heart stops beating is high when the concentration of potassium ions in his or her blood rises to 8.0 meq/L. On the contrary, a patient would suffer cramp, weakness, unwellness, and/or pain muscles when the concentration of potassium ions in his or her blood drops to 2.5-3 mEq/L. The patient might suffer fetal cardiac arrhythmia and/or respiratory failure when the concentration of potassium ions in his or her blood is lower than 2.5 mEq/L.

An early patient can only rely on a blood test to check the concentration of potassium ions in his or her blood. In such a blood test, the patient's blood is drawn with a syringe and tested with equipment. It causes pain to draw the blood. Moreover, it takes time to test the blood, and time is a luxury that an emergency patient does have. Researches show that a delay treatment could impose a risk of sudden cardiac death.

An electrocardiography ("ECG") records changes in voltage caused by changes in heartbeat. ECG signals are taken in non-intrusive manners. Studies show that ECG signals exhibit non-linear curves and shapes of waves and gaps between waves in ECG are directly related to electrocardiac properties. Hence, ECG is deemed a necessary tool for diagnose. However, in early days, the precision of researches did not meet requirements from cardiologists. Recently, artificial intelligence ("AI") based on deep learning is getting attention in various medical fields. AI based on deep learning diagnoses as well as medical specialists. To solve problems with failure of conventional ECG-assisted diagnosing tools to effectively quantitate, "Development and Validations of a Deep-Learning Model to Screen for Hyperkalemia From the Electrocardiogram" is published in Jama Cardiology for example. In that study, by development and verification of a deep-learning model, millions of ECGs are used to train a convolutional neural network ("CNN"). 2-lead (I and II) or 4-lead (I, II, V3 and V5) ECG is used to train the CNN to successfully detect a concentration of potassium ion in blood as low as 5.5 mEq/L or lower, with Area under the receiver operating characteristic curve (AUC) of 0.853-0.883, sensitivity of 88.9%-91.3%. Hence, it is proven that AI can be used to detect Hyperkalemia in ECG. However, it can only be used to determine whether a concentration of potassium ions in blood is higher or lower than 5.5 mEq/L. Hence, it can only be used to detect hyperkalemia. No other diagnoses can effectively be made based on different concentrations of potassium ions in blood.

As discussed above, different concentrations of potassium ions in blood require different treatments. The problems can be solved by converting ECG into concentrations of potassium ions in blood. Hence, it is an important issue to develop an ECG-assisted diagnosing tool to effectively quantitate concentrations of potassium ions in blood in the industry.

The present inventions is therefore intended to obviate or at least alleviate the problems encountered in the prior art.

SUMMARY OF INVENTION

It is an objective of the present inventions to provide a method and system to detect an abnormal concentration of potassium ions in blood based on ECG so that AI based on deep learning quantitates a concentration of potassium ions in blood based on ECG signals to allow medical personnel to provide proper treatments based on the actual concentration of potassium ions in blood.

It is another objective of the present inventions to provide a method and system to detect an abnormal concentration of potassium ions in blood that quickly determines a concentration of potassium ions in blood to allow medical personnel to provide proper treatments in time.

It is another objective of the present inventions to provide a method and system to detect a concentration of potassium ions in blood that executes long-term monitoring on a concentration of potassium ions in blood to allow medical personnel to intervene in time to reduce a risk of sudden cardiac death.

Other objectives, advantages and features of the present inventions will be apparent from the following descriptions referring to the attached drawings.

BRIEF DESCRIPTIONS OF DRAWINGS

The present inventions will be described via detailed illustrations of the preferred embodiment referring to the drawings wherein.

DETAILED DESCRIPTIONS OF PREFERRED EMBODIMENT

Figure 1:
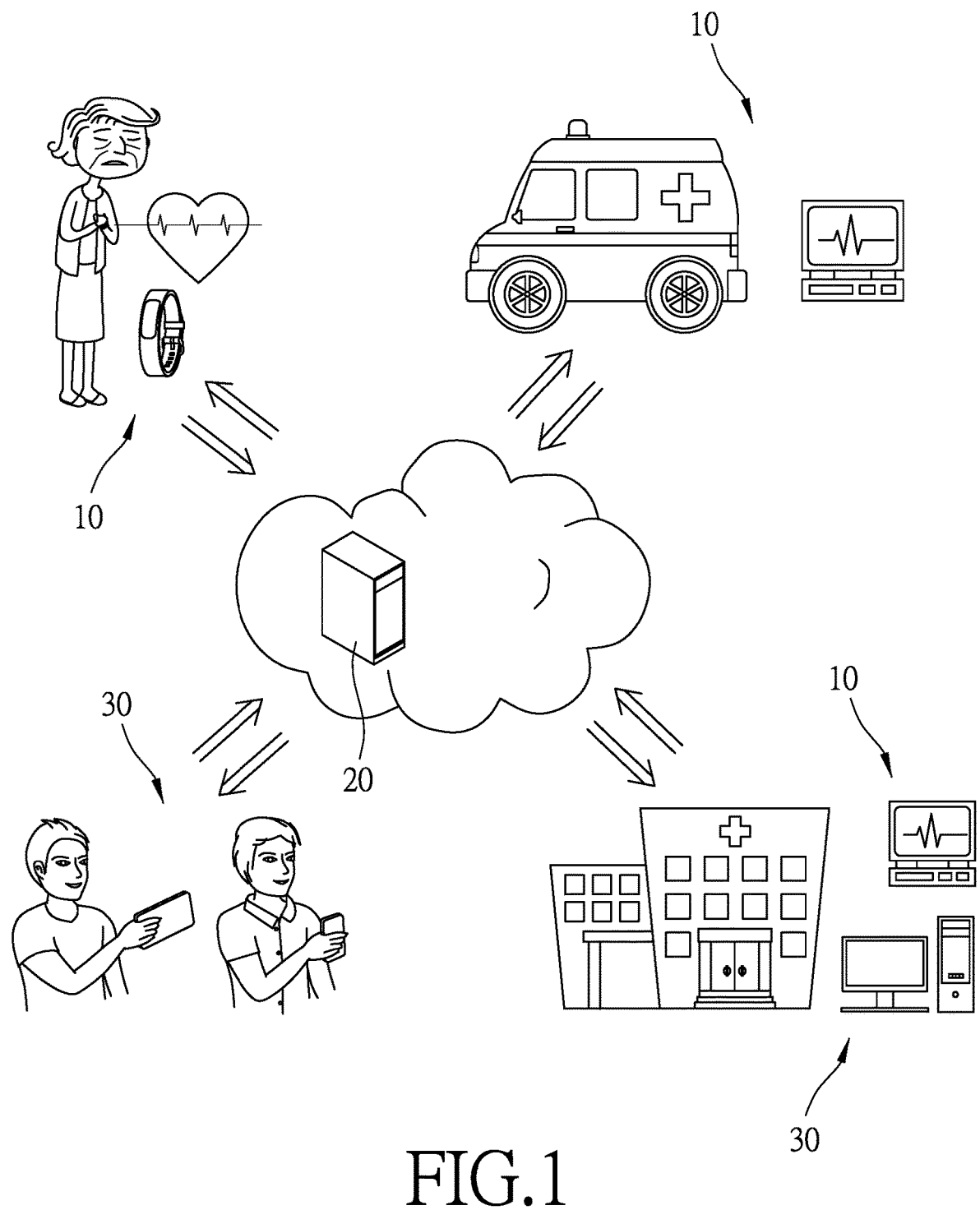
FIG. 1 is a sketch of a system in operation according to the preferred embodiment of the present invention.
Figure 2:
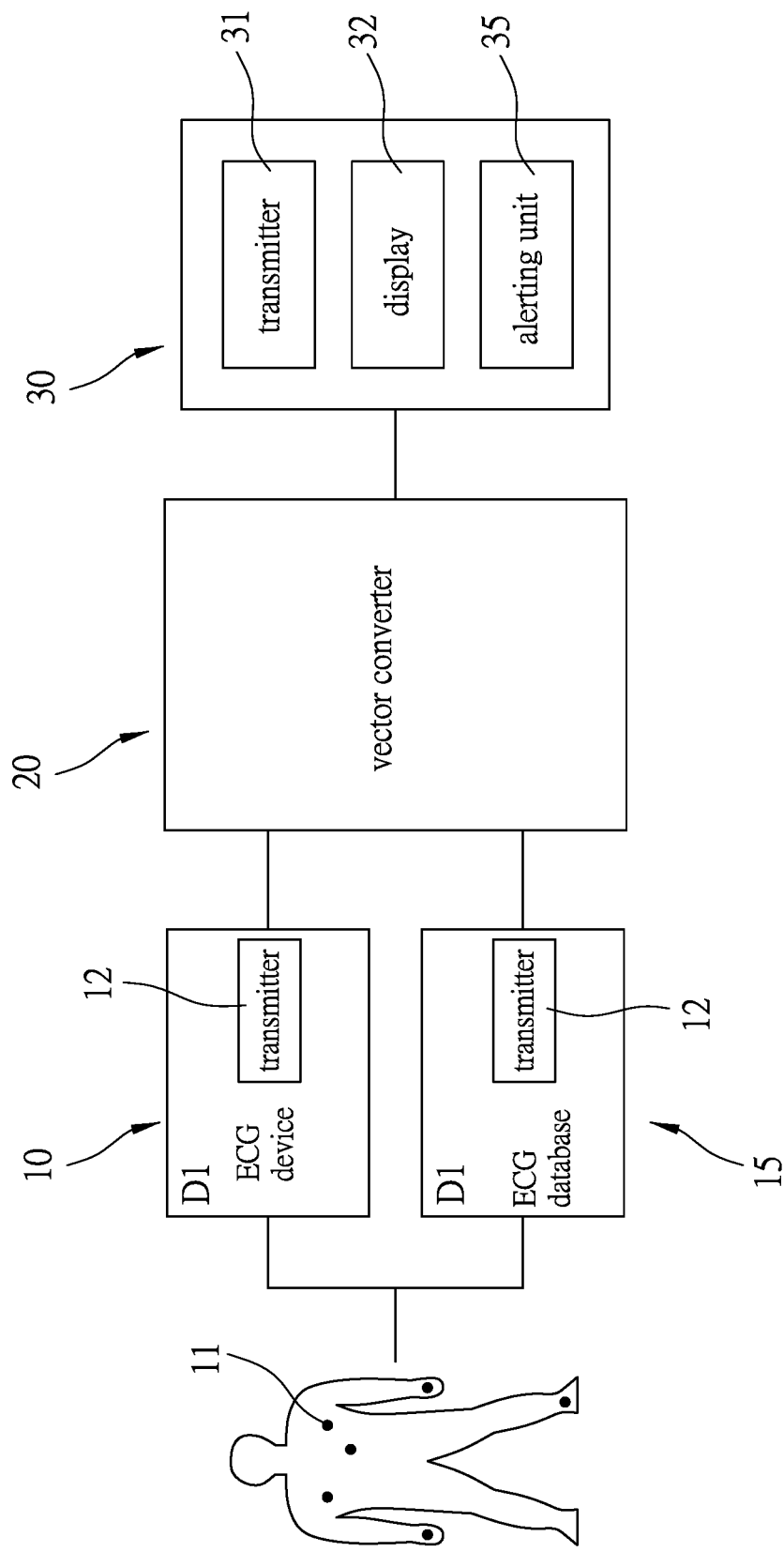
FIG. 2 is a block diagram of the system shown in FIG. 1

Referring to FIGS. 1 and 2, a system for quickly detecting abnormal concentrations of potassium ions in blood based on ECG includes an ECG device 10, a vector converter 20 and a monitor 30. The ECG device 10, the vector converter 20 and the monitor 30 can be made in one piece. Alternatively, any two of the ECG device 10, the vector converter 20 and the monitor 30 can be made in one piece. Alternatively, the ECG device 10, the vector converter 20 and the monitor 30 can be made in three pieces. Such pieces can be connected to one another by cables (such as Ether net) or in a wireless manner (such as Wi-Fi or mobile communication of 3G or higher) so that they are in communication of data with one another.

The ECG device 10 includes at least one electrode unit 11 and a transmitter 12. The electrode unit 11 can be attached to a human body to detect ECG signals. The electrode units 11 of the ECG device 10 can include at least one lead such as 1 lead, 2 leads, 3 leads, 6 leads, or 12 leads (Lead I, Lead II . . . Lead $V_6$) to provide ECG (D1) of a patient with a corresponding number of leads.

The transmitter 12 transmits the ECG (D1) of the patient to the vector converter 20 via cables or in a wireless manner. The ECG device 10 can be a wearable physiologic monitor that can be put on a patient to obtain the ECG (D1) of the patient. Thus, the physiologic status of the patient (such as a patient on an ambulance or a chronicle patient) can be monitored in a long-term manner. In an embodiment, the ECG device 10 can be an ECG database 15 for storing the ECG (D1) of the patient.

Figure 3:
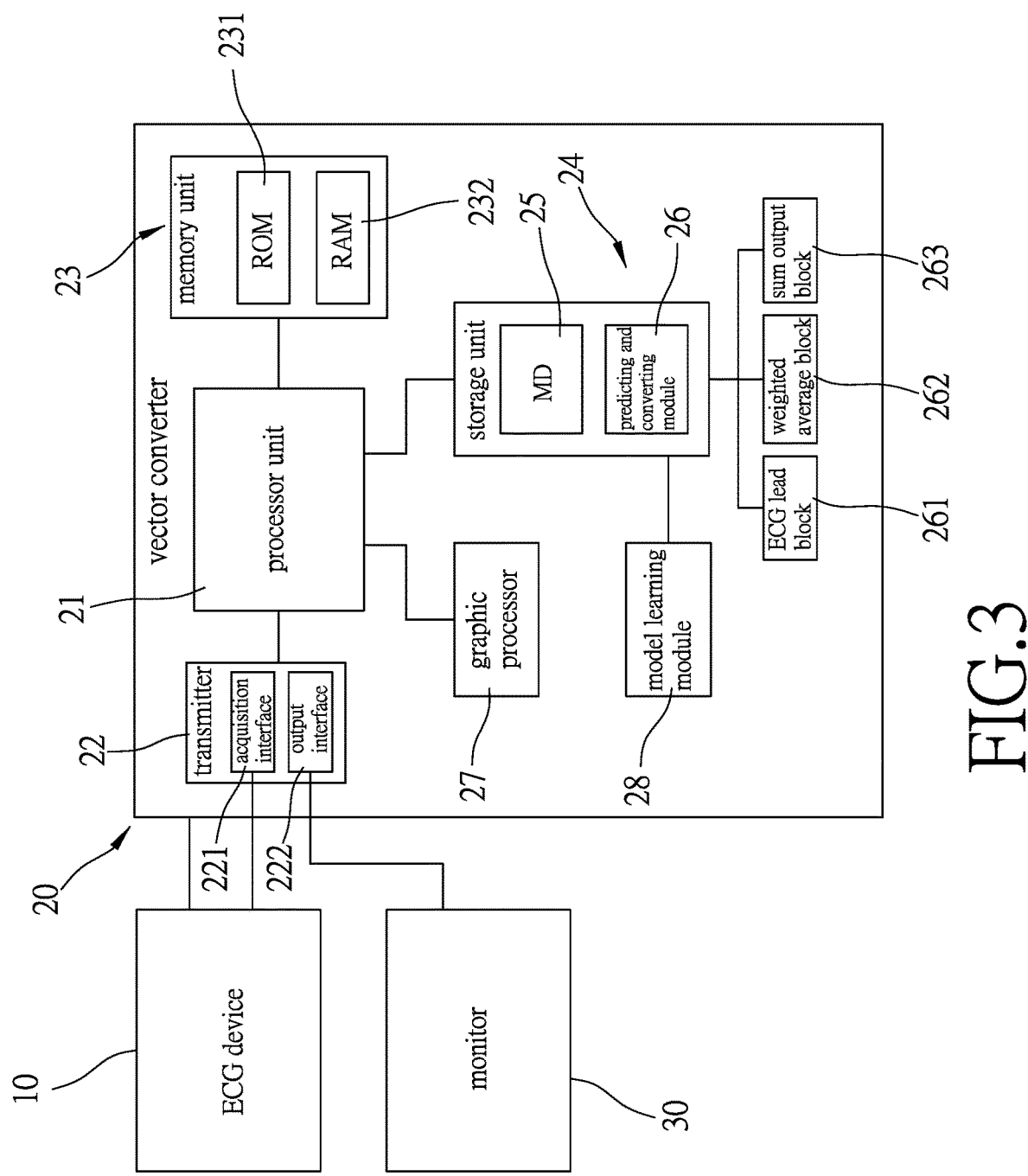
FIG. 3 is a bock diagram of a vector-converting device of the system shown in FIG. 1.

Referring to FIG. 3, the vector converter 20 can be a cloud server or another proper device (such as a server and a portable device) in communication with the ECG device 10 or a wearable physiologic monitor made in one piece with the ECG device 10. The vector converter 20 includes a processor unit 21, a transmitter 22, at least one memory unit 23 and at least one storage unit 24.

The processor unit 21 is used to execute various programs, commands and functions of the system. The processor unit 21 can be a central processing unit ("CPU") for example.

The transmitter 22 is connected to the processor unit 21. The transmitter 22 includes at least one acquisition interface 221 for connection to the ECG device 10 and at least one output interface 222 for connection to the monitor 30. Thus, the transmitter 22 is used to transmit data, pictures and commands between the vector converter 20 and the ECG device 10 or the monitor 30.

The memory unit 23 is electrically connected to the processor unit 21. The memory unit 23 includes a read only memory ("ROM") unit 231 and a random access memory ("RAM") unit 232. The memory unit 23 is used to store the programs and commands of the system and temporarily store an operation system or any other programs that are executed.

Figure 4:
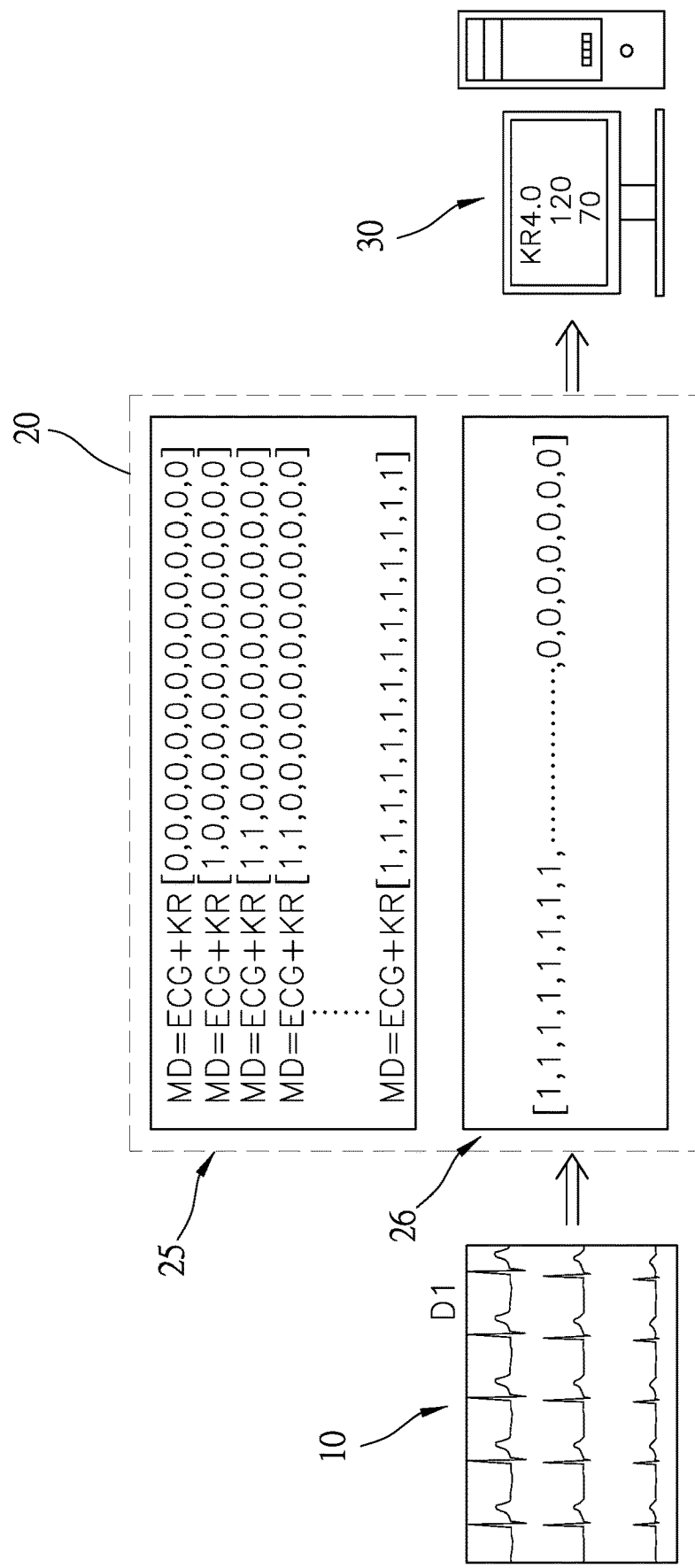
FIG. 4 is a sketch of a model-data module of the system illustrated in FIG. 1.

The storage unit 24 is connected to the processor unit 21 via cables or in a wireless manner. The storage unit 24 can be an internal storage device or an external storage device such as a hard disk drive ("HDD"), a solid state disc ("SSD") or an online hard drive. The storage unit 24 can store a model data module 25, a predicting and converting module 26 and various data for reference, comparison and execution. Thus, the ECG (D1) of the patient obtained by the ECG device 10 can be used to provide a predicted concentration of potassium ions in blood (KP) via comparison executed in the model data module 25 and calculation executed in the predicting and converting module 26 (FIG. 4).

The model data module 25 includes model data ("MD"). The MD includes at least one reference ECG and a corresponding reference concentration of potassium ions in blood ("KR"). The reference ECG includes at least one lead such as 1 lead, 2 leads, 3 leads, 6 leads and 12 leads. The MD can further include symptoms, medicine, age and sex of a patient so that the MD can be classified in detail. The KR is in a selected range of K1 to K2. For use in the following model structure, the value of KR is converted into a binary sequence of "0" and "1" and a q-value is used as an interval unit (q=0.01, 0.1 or 1). Thus, the selected range of the KR can be converted into a binary sequence that includes r digits (equation 1). Each KR can be converted into a binary sequence of "1" that includes i digits (equation 2). The KR and its binary sequence can be obtained from equations 1 and 2 as follows:

$$r=(K2-K1)/q \qquad \text{equation 1}$$

$$i=(KR-K1)/q \qquad \text{equation 2}$$

wherein i is the amount of "1" in the binary sequence that includes r digits.

For example, the selected range of the KR is 1.5 mEq/L (K1) to 7.5 mEq/L (K2), and a 0.1 mEq/L (q) is used as the interval unit. Thus, the selected range of the KR is converted to a binary sequence that includes 60 (r) digits. The selected range of the KR is 1.5+0.1i, wherein the amount (i) of "1" is 0, 1, 2, 3, . . . or 60. Thus, when the KR is 1.5 mEq/L, the amount (i) of "1" in its binary sequence is (1.5-1.5)/0.1=0, i.e., it does not include any "1." The binary sequence of the KR of 1.5 mEq/L is (0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0). Moreover, when the KR is 4.0 mEq/L, the amount of "1" in its binary sequence is (4.0-1.5)/0.1=25. The binary sequence of the KR of 4.0 mEq/L is (1, 1, 1, 1, 1, 1, 1, 1, 1, 1, 1, 1, 1, 1, 1, 1, 1, 1, 1, 1, 1, 1, 1, 1, 1, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0).

Figure 5:
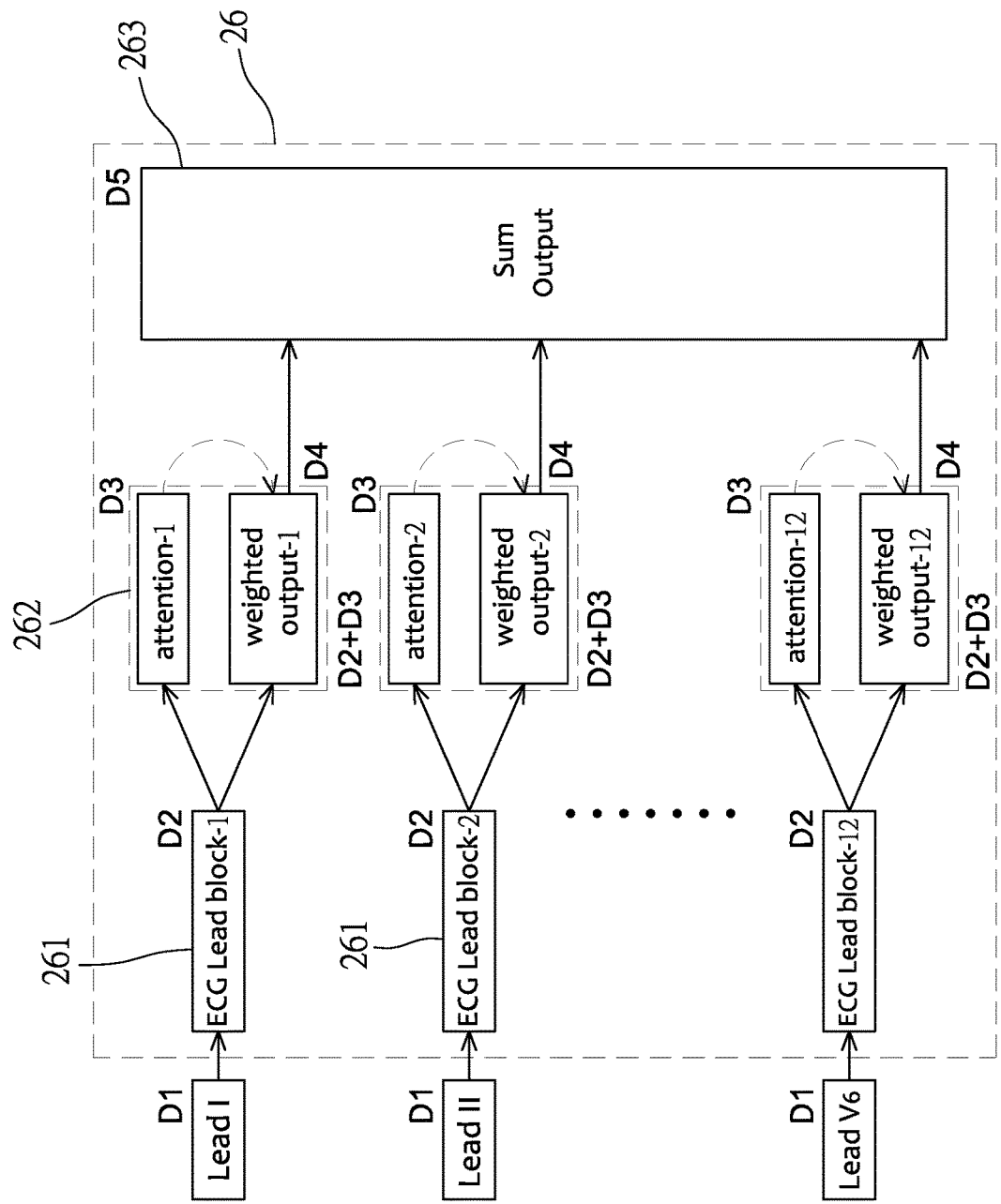
FIG. 5 is a sketch of a binary sequence converter of the system shown in FIG. 1.

The self-educating predicting and converting module 26 is a convolutional neural network ("CNN") selected from the third generation of AI such as a dense convolutional network. Referring to FIG. 5, the predicting and converting module 26 includes at least one ECG lead block 261, a weighted average block 262 (or "attentions block") and a sum output block 263. The ECG lead block 261 is a deep neural network with a sequence vector as an input so that each lead uses this structure to produce a guided predicted value (D2).

Figure 6:
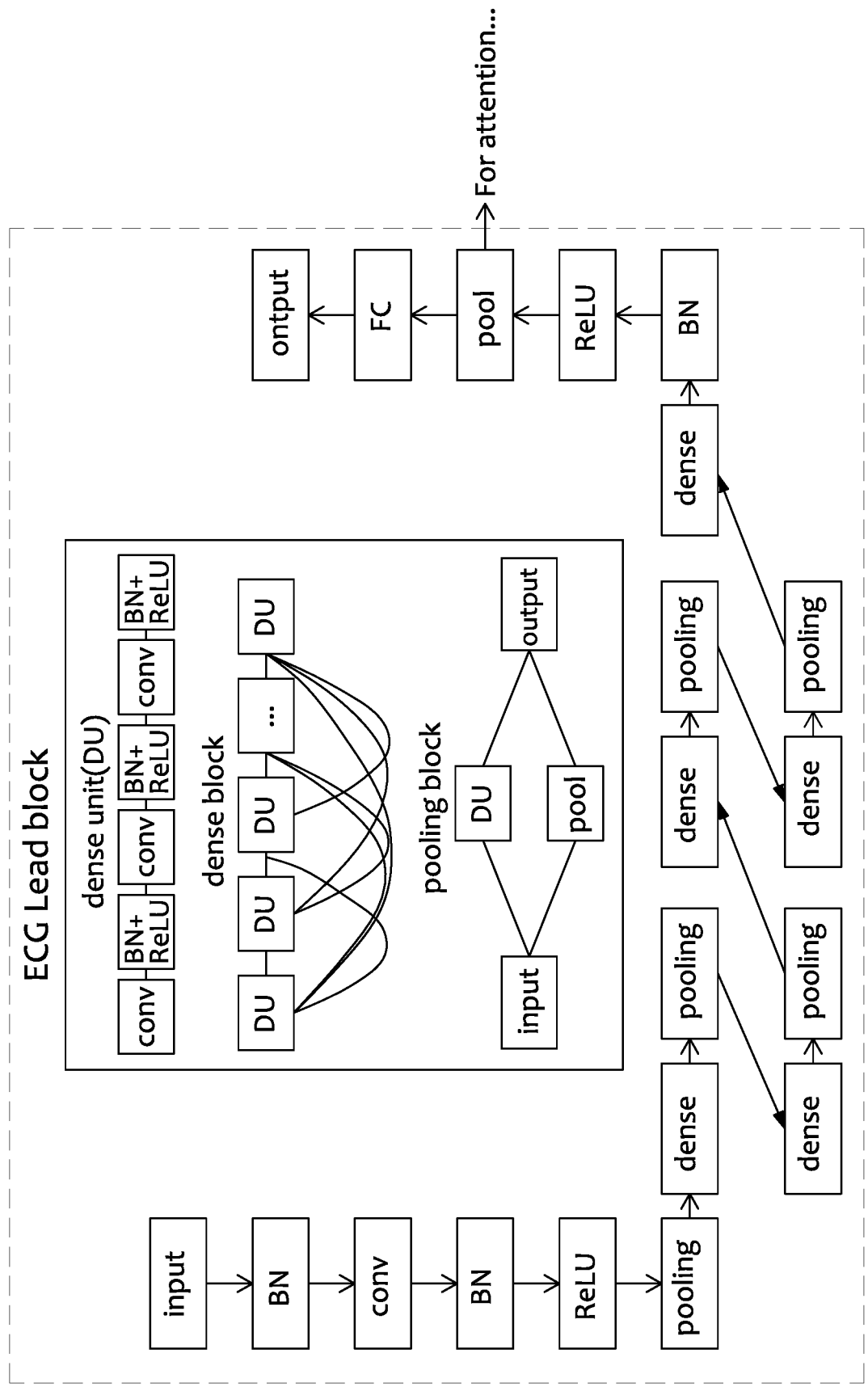
FIG. 6 is a block diagram of an ECG lead block of the binary sequence converter of the system shown in FIG. 1.

For example, referring to FIG. 6, a structure is designed based on the DenseNet algorithm. The core structure is a dense unit ("DU"). The dense unit is a continuous "first convolution→batch norm ("BN")→rectified linear unit ("ReLU")→second convolution→BN→ReLU." The first convolution includes 4K 1×1 convolutors. The second convolution includes K 3×1 convolutors. K is common constant for the models. Preferably, K is 32 in the present application.

Then, dense blocks are built by overlapping dense units. In each dense block, the connection of all the dense units to one another is dense connection. In each dense block, any dense unit can receive information from any previous dense unit. To increase the diversity of the predicting and converting module 26, an additional pooling block is used to compensate drawbacks related to failure of each dense block to execute dimensional reduction. The pooling block is made by overlapping dense units with a pool. Each dense unit includes a stride of 2, and so does the pool. The ECG lead block 261 is made by connecting the dense blocks to the pooling block. Initially, the structure of the network of the predicting and converting module 26 includes a continuous "BN→convolution→BN→ReLU→pool". The convolution includes 2K 7×1 convolutors (stride of 2×1). The pool uses a 3×1 pooling element (stride of 2×1) to execute dimensional reduction. Then, "dense block→transitions block→dense block→transitions block→dense block→transitions block→dense block" is interconnected. Sequentially, the dense blocks include 3, 3, 6, 6, 3 dense units. Then, a batch norm and a rectified linear unit are used to process the result before global-average pooling is used to execute final data integration. Finally, a fully connected layer ("FC") is used as a final output for the model.

After the ECG lead block 261, for each lead, the guided predicted value (D2) will include an eigenvector with a length of N and an individual predicted result with a length of 1. Then, the weighted average block 262 is used to execute weighted prediction on the eigenvector.

Figure 7:
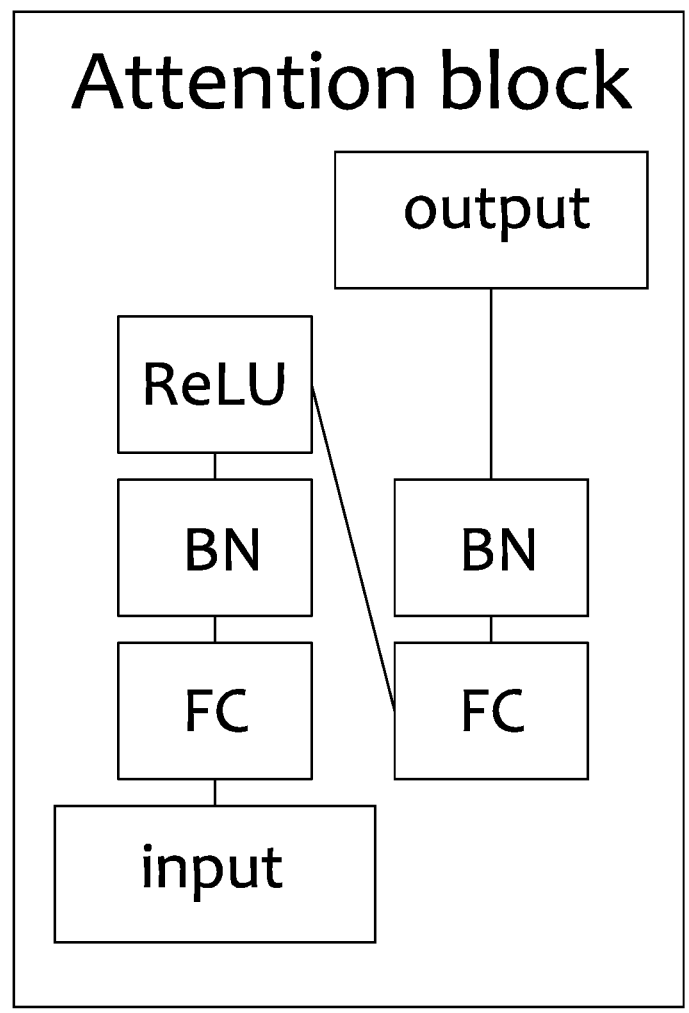
FIG. 7 is a block diagram of an attention block of the binary sequence converter of the system shown in FIG. 1.

For example, referring to FIG. 7, the structure of the weighted average block 262 is "FC→BN→ReLU→FC→BN". Finally, each weighted average block 262 produces a weighted value D3. The weighted average block 262 turn the 12 leads into outputs that are processed in a Sofrmax function so that their sum is 100%. Then, weighted averaging is imposed on the weight and the original guided predicted value (D2) of the ECG lead block 261 to provide an overall estimated value (D4).

Figure 8:
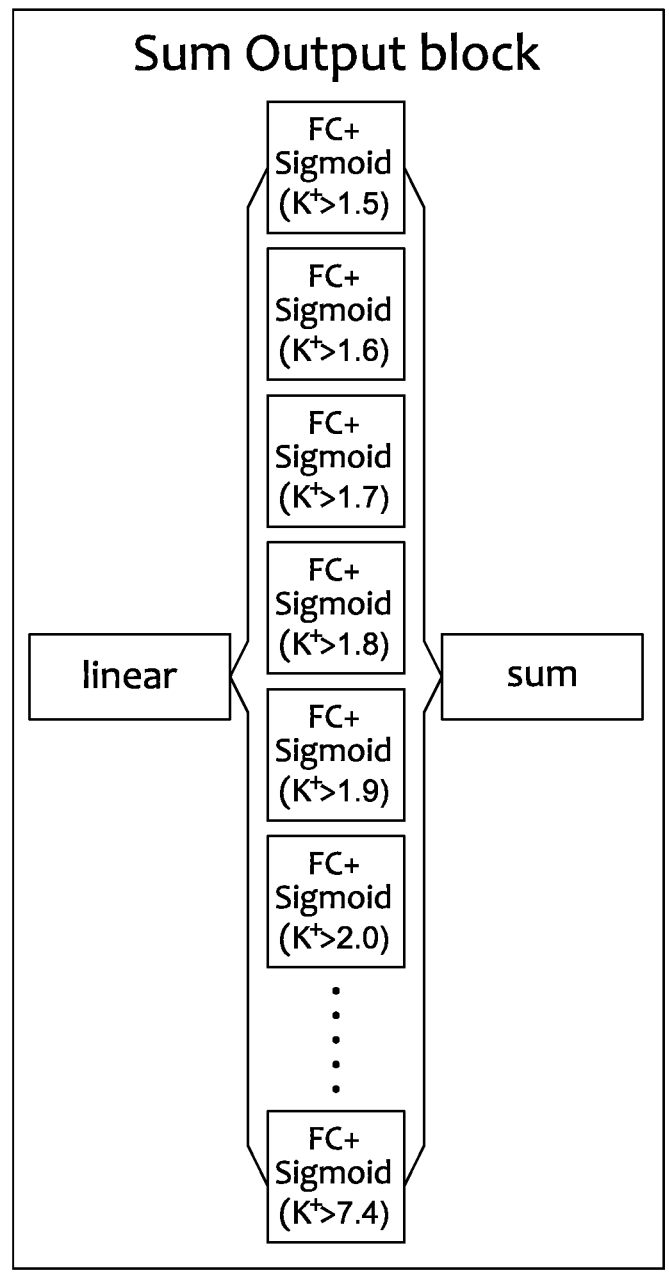
FIG. 8 is a block diagram of a sum output block of the binary sequence converter of the system shown in FIG. 1.

After the ECG lead block 261 and the weighted average block 262, the KR is turned to a binary sequence of "0" and "1." Hence, the structure of the sum output block 263 is used to execute result prediction. Referring to FIG. 8, the operation of the sum output block 263 is based on an assumption that the reference concentration of potassium ions in blood is 1.5 to 7.5, 0.1 is used as a unit for coding. Thus, r (such as 60) structures of "FC→Sigmoid output" are built. The final prediction by the model is 60 probability vectors (D5) of 0 to 1, including i digits of "1."

With the use of the ECG lead block 261, the weighted average block 262 and the sum output block 263 of the predicting and converting module 26, there are provided r (such as 60) probability vectors 60 of "0" to "1", including i digits of "1." A predicted KP is provided by using an equation 3. The predicted KP is transferred to the output interface 222 of the transmitter 22 of the vector converter 20, and then transferred to the monitor 30.

$$KP = K1 + qi \qquad \text{equation (3)}$$

In a proper embodiment, the vector converter 20 further includes a graphic processor unit ("GPU") 27 connected to the processor unit 21. With the GPU 27 is used to execute graphic calculation at high speed through analysis, deep learning and machine learning.

In a proper embodiment, the vector converter 20 further includes a model-learning module 28 in the form of a convolutional neural network to provide a new MD for use in diagnose. The model-learning module 28 uses a convolutional neural network to identify eigenvalues of the ECG in an unsupervised manner to learn. In the learning process, the convolutional neural network of the model-learning module 28 can execute algorithms that are known and adjust network parameters (such as weights and deviations). The MD (structural data and learned weights) formed by the model-learning module 28, the model data module 25 and the predicting and converting module 26 are stored in the storage unit 24.

As discussed above, the model-learning module 28 can train the deep learning model by backpropagation that is known. In the learning process, at first, a loss function is defined to the sum of cross-entropies, wherein $p_i$ is a final probability vector (D5), and $y_i$ is a binary sequence of the KR after the coding:

$$loss = \sum_{i=1}^{60} y_i \log p_i \qquad \text{equation 4}$$

In training, an original digital sequence of potential signals is randomly cut into segments with a length of $k \times 2^n$ (n is 6 for example). For example, to build the model data module 25, every period of 2 milliseconds is used to record a signal, and the recording lasts for 10 seconds so that the length of the sequence is 5000. A digital sequence with a length of 1024 (k=16) can be cut for the training of the MD. Then, the training of the MD can begin. For example, Adam that exhibits an initial learning rate of 0.001 is used to optimize the learning. The parameters are set to be the standard parameters ($\beta 1$ is 0.9, and $\beta 2$ is 0.999). The length is reduced by 10 folds when the overall loss stops dropping. The foregoing process is repeated for 3 times, and a regularization coefficient L2 is set to be 10'.

In training, a batch of n (such as 50) is produced randomly in each round of training, and oversampling is used to set weights for sampling according to the amount of the data. Thus, balance is achieved among the groups of K+≤2.5, 2.5<K+≤3.5, 3.5<K+<5.5, 5.5≤K+<6.5 and 6.5≤K+.

In addition to the above-mentioned methods, a few data augmentation methods can be used to increase the precision of the MD. For example, in each round of training, the six of the twelve weighted average blocks 262 of the predicting and converting module 26 are reset to be 0. Thus, only half of each ECG is visible in the training of the MD.

In the training process, a null vector of a sequence with a length of 50 is used as a template to randomly shield waves in uncertain regions of the ECG.

In the training process, the number of heart beats is reset to be 80% to 120% of the original number of heart beats. Then, a sequence with a length of $k \times 2^6$ is drawn from the sequence with the adjusted size and used for training.

In the training of the model data module 25, if the predicted KP provided from the predicted vector converter 20 is a probability vector with a length of N wherein the value of the probability vector is 0 to 1, and the range of the KR is 1.5 to 7.5, and 0.1 is used as the unit for coding, then the predicted KP is (1, 1, 1, 1, 1, 1, 1, 1, 1, 0.9, 0.8, 0.7, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0, 0), and this vector is accumulated and then divided by 10 and added by 1.5 to be 2.64 (mEq/L). Moreover, since the calculation is based on the cut digital sequences in the training of the vector converter 20, the original ECG signals (D1) must be cut into digital vectors with a length of k×26 by a constant internal, and multiple predicted results are averaged to provide a final predicted result, e.g., an average is provided from the first 1024 digital sequences and the last 1024 digital sequences.

The model data module 25, the predicting and converting module 26 and the model-learning module 28 of the vector converter 20 can be stored in a same storage unit 24 or different storage units 24.

Referring to FIGS. 1 and 2, the monitor 30 includes a transmitter 31 and a display unit 32. The transmitter 31 receives detected values and/or ECG signals from the vector converter 20 via cables or in a wireless manner. The display unit 32 shows the predicted KP and/or ECG produced from the ECG signals (D1) to allow medical personnel to provide treatments to patients according to the actual concentrations of potassium ions in blood and allow the medical personnel to read the predicted KP. In a proper embodiment, the monitor 30 further includes an alerting unit 35. The alerting unit 35 transmits the detected predicted KP and/or the ECG produced from the ECG signals (D1) to emergency personnel, responsible doctors or remote monitors to allow the medical personnel to monitor and intervene in time to reduce risks of sudden cardiac death.

Figure 9:
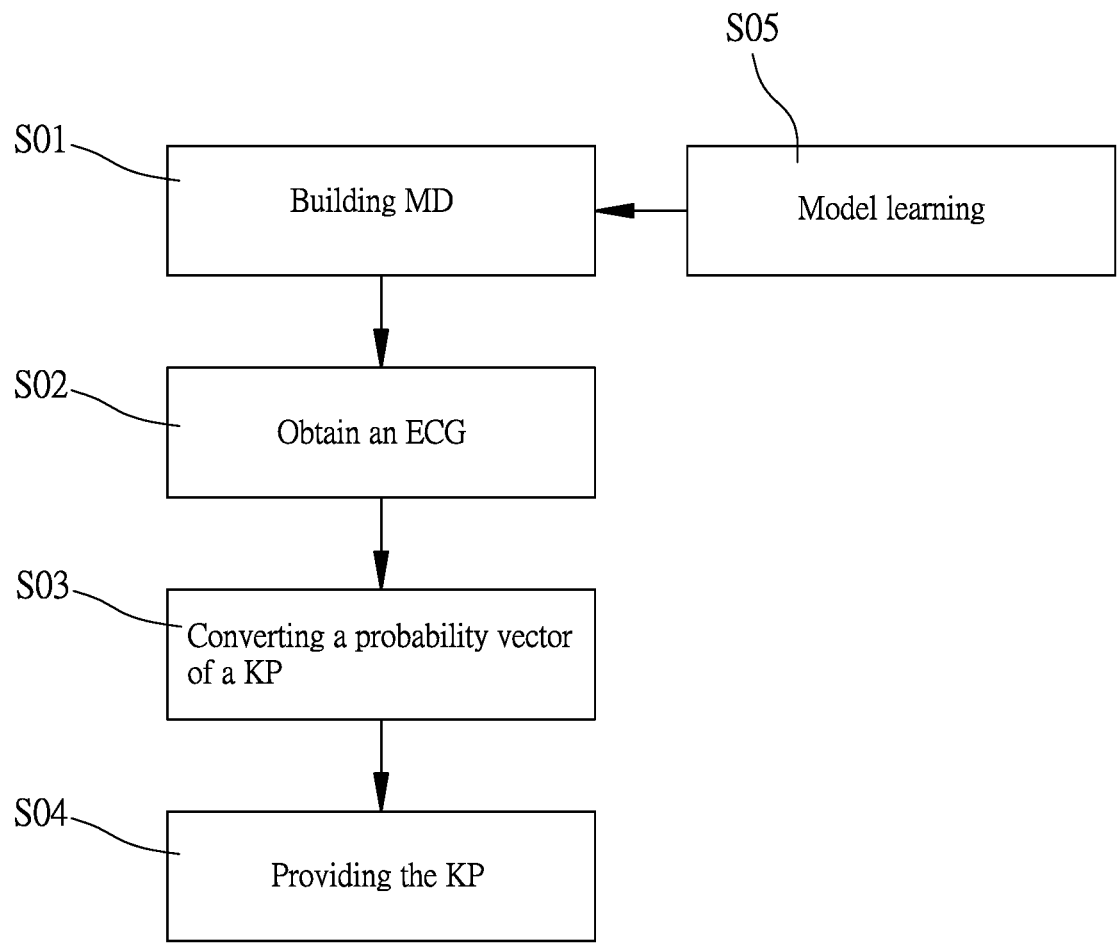
FIG. 9 is a flow chart of a method for quickly detecting an abnormal concentration of potassium ions in blood from an electrocardiogram executed in the system shown in FIG. 1.

The present invention further provides a method executed in the above-mentioned system. Referring to FIG. 9, at S01, at least one MD is built. The MD uses an ECG to provide a corresponding KR in blood test. The KR is in a selected range of K1 to K2, with an interval unit set to be q. The selected range of the KR is converted to a binary sequence of r digits of "0" and "1." The KR of each unit can be converted to a binary sequence of i digits of "1". The conversion is achieved by equations 1 and 2 as follows:

$$r=(K2-K1)/q \qquad \text{equation 1}$$

$$i=(KR-K1)/q \qquad \text{equation 2}$$

At S02, at least one ECG of a monitored person is provided.

At S03, a probability vector of KP is converted. The ECG of the monitored person is used to conversion that includes a guided prediction with a convolutional neural network, weighted average and sum output. The guided prediction is used to enter the ECG of the monitored person as a sequence vector and produce a guided predicted value. Then, the weighted average is used to execute weighted prediction, and the guided predicted value is subject to weighting and averaging to provide an overall estimated value. Then, the sum output is used for result prediction based on the KR of the binary sequence in the MD. Thus, a probability vector in the form of a binary sequence of r digits, including i digits of "1."

At S04, a predicted KP is provided. After the probability vector of the ECG of the monitored person is provided, the probability vector is converted into a predicted KP according an equation 3 as follows:

$$KP=K1+qi \qquad \text{equation 3}$$

The method further includes model learning that uses a convolutional neural network to identify the eigenvalue of an ECG in an unsupervised manner. The convolutional neural network used in the model learning can execute algorithms that are known and adjust network parameters to produce new MD for diagnose.

The present invention has been described via the illustrations of the preferred embodiment. Those skilled in the art can derive variations from the preferred embodiment without departing from the scope of the present invention. Therefore, the preferred embodiment shall not limit the scope of the present inventions defined in the claims.

The invention claimed is:

1. A method for quickly detecting an abnormal concentration of potassium ions in blood from an electrocardiogram comprising the steps of:
building at least model data (MD) by using at least one reference ECG to provide a corresponding reference concentration of potassium in blood (KR), wherein the reference concentration of potassium ions in blood is in a selected range of K1 to K2, with an interval unit of q, wherein the selected range of the reference concentration of potassium ions in blood is converted into a binary sequence that comprises r digits of "0" and "1", wherein the reference concentration of potassium in blood (KR) is converted into a binary sequence that comprises i digits of "1" according to first and second equations:

$$r=(K2-K1)/q \qquad \text{the first equation; and}$$

$$i=(KR-K1)/q \qquad \text{the second equation;}$$

providing an ECG of a monitored person;
converting the ECG of the monitored person into a probability vector that comprises i digits of "1" in a binary sequence that comprises r digits by operating a model in the form of a convolutional neural network based on the reference concentration of potassium ions in blood (KR) of the binary sequence of the model data; and
converting the probability vector into a predicted concentration of potassium ions in blood (KP) by a third equation as follows:

$$KP=K1+qi \qquad \text{the third equation.}$$

2. The method according to claim 1, wherein the ECG of the monitored person is derived from ECG signals with 12 leads.

3. The method according to claim 1, further comprising the step of model learning that learns by using a convolutional neural network to identify the eigenvalue of an ECG in an unsupervised manner to produce new MD for diagnose.

4. A system for quickly detecting abnormal concentration of potassium ions in blood from electrocardiogram comprising at least one vector converter comprising a transmitter, at least one memory unit, at least one storage unit and a processor unit connected to the transmitter, the memory unit and the storage unit, wherein the storage unit comprises a model data module and a predicting and converting module, wherein the model data module comprises model data comprising an ECG and a corresponding reference concentration of potassium ions in blood, wherein the predicting and converting module executes the method of claim 1 to convert the ECG of the monitored person into the corresponding predicted concentration of potassium ions in blood.

5. The system according to claim 4, further comprising at least one ECG device connected to the vector converter and at least one monitor connected to the vector converter so that the vector convertor converts the ECG of the monitored person provided by the ECG device into the predicted concentration of potassium ions in blood, and shows the predicted concentration of potassium ions in blood on the monitor.

6. The system according to claim 5, wherein the transmitter comprises at least one acquisition interface connected to the ECG device and at least one output interface connected to the monitor.

7. The system according to claim 5, wherein the vector converter is a wearable physiologic monitor made in one piece with the ECG device.

8. The system according to claim 5, wherein the ECG device, the vector converter and the monitor are made in one piece.

9. The system according to claim 5, wherein the monitor comprises a display unit for showing a predicted concentration of potassium ions in blood and an ECG derived from ECG signals.

10. The system according to claim 5, wherein the monitor further comprises an alerting unit for transmitting the predicted concentration of potassium ions in blood and the ECG derived from the ECG signals to another monitor.

11. The system according to claim 4, wherein the vector converter further comprises a graphic processor unit connected to the processor unit to increase speed of calculation.

12. The system according to claim 4, wherein the vector converter further comprises a model-learning module that learns by using a convolutional neural network to identify an ECG in an unsupervised manner.

13. The system according to claim 12, wherein the model data module, the predicting and converting module and the model-learning module of the vector converter are stored in a same storage unit.

14. The system according to claim 4, wherein the memory unit comprises a read only memory unit and a random access memory unit for storing programs and commands of the system and for temporarily storing an operation system and any other programs that are executed.

15. The system according to claim 4, wherein the storage unit is connected to the processor unit via cables or in a wireless manner.

16. The system according to claim 15, wherein the storage unit is an internal storage device or an external storage device.

17. The system according to claim 16, wherein the vector converter is an online server.

18. A predicting and converting module for providing a predicted concentration of potassium ions in blood from an ECG, making a computer execute the following tasks:
- using a convolutional neural network to build model data that comprises an ECG and a corresponding concentration of potassium ions in blood and to convert the concentration of potassium ions in blood into a reference concentration of potassium ions in blood in the form of a binary sequence;
- obtaining an ECG of a monitored person from an ECG device and using the convolutional neural network to derive a probability vector from the ECG;
- converting the probability vector into a predicted concentration of potassium ions in blood according to the binary sequence of the reference concentration of potassium ions in blood; and
- showing results of analysis of the predicted concentration of potassium ions in blood and using a monitor to control and process the results.

19. The predicting and converting module according to claim 18, wherein the building of the model data further comprises learning by using a convolutional neural network to identify eigenvalues of the ECG in an unsupervised manner.

* * * * *